United States Patent
Eaton

(10) Patent No.: US 10,478,214 B2
(45) Date of Patent: Nov. 19, 2019

(54) BALLOON CATHETER WITH LITHOTRIPSY AMPLIFICATION SYSTEM

(71) Applicant: Cook Medical Technologies LLC, Bloomington, IN (US)

(72) Inventor: Elizabeth A Eaton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 641 days.

(21) Appl. No.: 14/534,524

(22) Filed: Nov. 6, 2014

(65) Prior Publication Data

US 2015/0127034 A1 May 7, 2015

Related U.S. Application Data

(60) Provisional application No. 61/901,103, filed on Nov. 7, 2013.

(51) Int. Cl.
*A61B 17/22* (2006.01)
*A61B 17/3207* (2006.01)

(52) U.S. Cl.
CPC ......... *A61B 17/320758* (2013.01); *A61B 2017/320716* (2013.01); *A61B 2017/320733* (2013.01); *A61B 2017/320766* (2013.01)

(58) Field of Classification Search
CPC .... A61B 17/320741; A61B 17/320758; A61B 17/320725; A61B 17/3207; A61B 17/22012
See application file for complete search history.

(56) References Cited

U.S. PATENT DOCUMENTS

| | | | |
|---|---|---|---|
| 2,227,727 A | 1/1941 | Leggiadro | |
| 2,933,088 A | 4/1960 | Winner et al. | |
| 3,636,948 A | 1/1972 | Atchley | |
| 5,443,078 A * | 8/1995 | Uflacker | A61B 17/22012 600/585 |
| 5,722,979 A | 3/1998 | Kusleika | |

(Continued)

FOREIGN PATENT DOCUMENTS

| | | |
|---|---|---|
| WO | WO 2005/115545 A1 | 12/2005 |
| WO | WO 2014/163955 A1 | 10/2014 |

OTHER PUBLICATIONS

Extended European Search Report, pp. 1-7 dated Jan. 11, 2017, issued in European Patent Application No. 16187667.7, European Patent Office, The Hague, The Netherlands.

(Continued)

*Primary Examiner* — Kathleen S Holwerda
*Assistant Examiner* — Christina C Lauer
(74) *Attorney, Agent, or Firm* — Brinks Gilson & Lione

(57) ABSTRACT

An intraluminal scoring system for expanding an opening within an intraluminal passage includes a balloon catheter which is positioned alongside plaque lining a wall of the intraluminal passage. A wire is positioned between the balloon and the plaque so that the inflation of the balloon restricts the wire between the balloon and the plaque. After the balloon is inflated, a mechanical vibration is induced in the proximal end of the wire by a lithotripter actuator. The vibration travels through the wire to the distal portion, causing the wire to impact the plaque lining the wall of the passage causing scoring, compression, or fragmentation of the plaque.

21 Claims, 4 Drawing Sheets

(56) References Cited

U.S. PATENT DOCUMENTS

| | | | |
|---|---|---|---|
| 5,827,304 | A | 10/1998 | Hart |
| 6,440,061 | B1 | 8/2002 | Wenner et al. |
| 7,479,148 | B2 | 1/2009 | Beaupré |
| 7,682,366 | B2 | 3/2010 | Sakurai et al. |
| 2002/0010489 | A1 | 1/2002 | Grayzel et al. |
| 2002/0165558 | A1 | 11/2002 | Engel |
| 2003/0040754 | A1 | 2/2003 | Mitchell et al. |
| 2003/0229370 | A1 | 12/2003 | Miller |
| 2005/0021071 | A1 | 1/2005 | Konstantino et al. |
| 2006/0111704 | A1* | 5/2006 | Brenneman ............ A61B 17/11 606/41 |
| 2007/0282301 | A1* | 12/2007 | Segalescu ......... A61M 25/1002 604/509 |
| 2009/0118741 | A1 | 5/2009 | Lebet |
| 2010/0036294 | A1 | 2/2010 | Mantell et al. |
| 2010/0274231 | A1 | 10/2010 | Pravong et al. |
| 2014/0277002 | A1* | 9/2014 | Grace ................... A61B 17/22 606/159 |

OTHER PUBLICATIONS

European Search Report, dated Mar. 12, 2015, pp. 1-5, European Patent Application No. 14 27 5226, European Patent Office, The Hague.

Medical Device Daily™, The Medical Technology News Source, vol. 18, No. 20, Jan. 30, 2014, 2 pp.

Chinese Office Action with English translation, dated Nov. 9, 2017, pp. 1-11, issued in Chinese Patent Application Serial No. 201410637148.6, State Intellectual Property Office of P.R. China, Beijing, P.R. China.

Chinese Office Action with English translation, dated Nov. 28, 2018, pp. 1-12, issued in Chinese Patent Application Serial No. 201410637148.6, State Intellectual Property Office of P.R. China, Beijing, P.R. China.

Chinese Office Action with English translation, dated Jun. 12, 2018, pp. 1-10, issued in Chinese Patent Application Serial No. 201410637148.6, State Intellectual Property Office of P.R. China, Beijing, P.R. China.

* cited by examiner

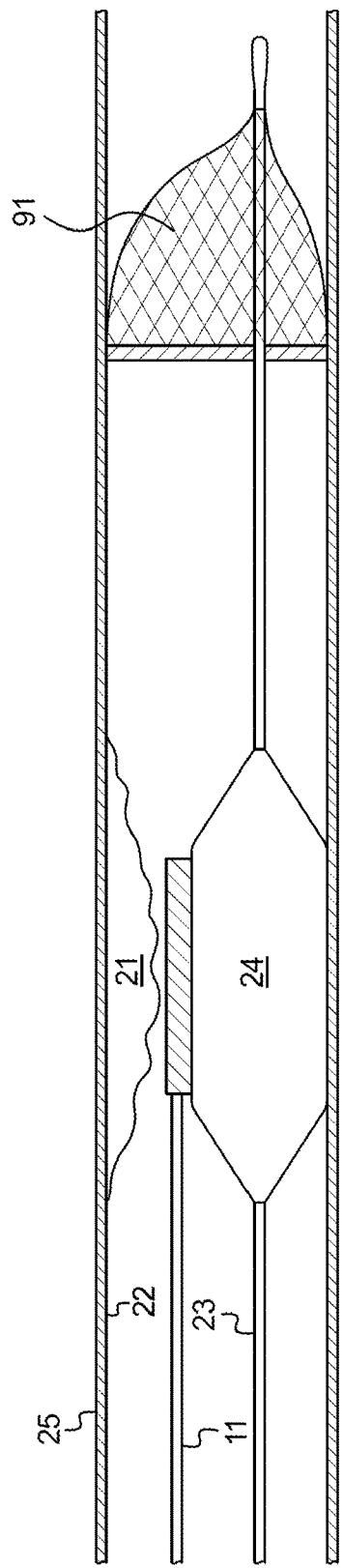

BALLOON CATHETER WITH LITHOTRIPSY AMPLIFICATION SYSTEM

CROSS-REFERENCE TO RELATED APPLICATIONS

The present disclosure is related to and claims all benefit pursuant to 35 U.S.C. § 119 of U.S. Provisional Application Ser. No. 61/901,103, filed Nov. 7, 2013, which is incorporated by reference in its entirety.

BACKGROUND

The field of the present invention relates to balloon catheters for expanding an opening within an intraluminal passage, such as a blood vessel or an artery.

The use of a balloon catheter to expand openings within blood vessels or arteries is well known within the field of vascular surgery. One example of their use is in angioplasty, where plaque has built up on the walls of an artery restricting blood flow. In this procedure, a catheter with a balloon is inserted into the artery and the balloon is inflated with a saline solution to compress the plaque against the artery wall, thereby enlarging the opening. However, if the plaque has hardened, it can be difficult for a simple balloon to achieve the desired compression. Furthermore, if the balloon is over-inflated to achieve the desired compression, it can burst causing complications to the patient.

To overcome this problem, in some situations, balloons with scoring edges are used to focus pressure on a single point and achieve better compression of the plaque, or to achieve similar compression with less inflation pressure. Despite the use of this technique, a scoring balloon may be insufficient to achieve the desired compression of plaque. Furthermore, the addition of a scoring edge increases the cross-sectional area of the catheter, which limits it use in small or stenotic blood vessels.

SUMMARY

An intraluminal scoring system may be used within an intraluminal passage to enlarge the passage by compressing, scoring, or fragmenting plaque lining the wall of passage. It is also desirable to enlarge the intraluminal passage while applying minimal pressure to inflate the balloon.

In view of this, the scoring system includes a balloon catheter, a wire, and a lithotripter actuator. The proximal end of the wire is attached to the lithotripter actuator while the distal end of the wire is positioned near or alongside the deflated balloon in the passage. Once the balloon has been inflated, the movement of the wire in the intraluminal passage is constrained between the outer surface of the balloon and plaque which lines the wall of passage. Once the balloon is inflated, the lithotripter actuator may be activated, transmitting mechanical energy in the form of a vibration from the proximal end of the wire and through the wire toward its distal end. The vibration of the distal end of the wire causes the wire to impact the plaque lining the wall of the intraluminal passage, causing compression, scoring, or fragmentation.

A possible advantage of the present scoring system is that the wire's vibration may more effectively cause scoring or fragmentation of the plaque lining the wall of the intraluminal passage than traditional scoring balloon catheters. In urology, the introduction of a mechanical vibration has proven effective in breaking apart calcified masses, such as kidney stones. Similarly, mechanical vibration of a wire against plaque in an intraluminal passage may be more effective in scoring plaque than a simple scoring edge pressed against the plaque by a balloon.

Another possible advantage of the scoring system is that the balloon may not need to be inflated to the same size or pressure as an equivalent balloon catheter performing the same compression of plaque lining the wall of a passage. As a result of this decreased inflation pressure, the wall of the balloon for the device may be substantially thinner. Thinner balloon walls will also allow the balloon catheter to have a substantially smaller deflated cross-section, allowing the catheter to be deployed in narrower intraluminal passages.

BRIEF DESCRIPTION OF SEVERAL VIEWS OF THE DRAWINGS

The invention may be more fully understood by reading the following description in conjunction with the drawings, in which:

FIG. 9 is a side plan view of a scoring system within an intraluminal passage, showing a balloon catheter, a wire, and an embolic protection device.

DETAILED DESCRIPTION

Figure 1:
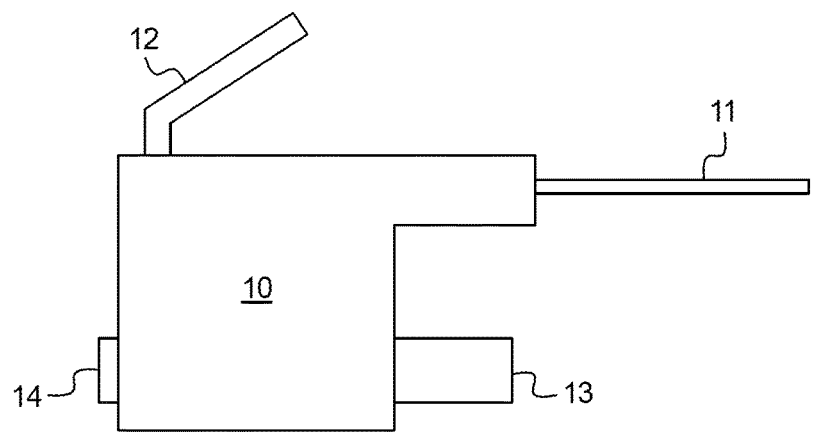
FIG. 1 is a side plan view of a lithotripter actuation device.
Figure 2:
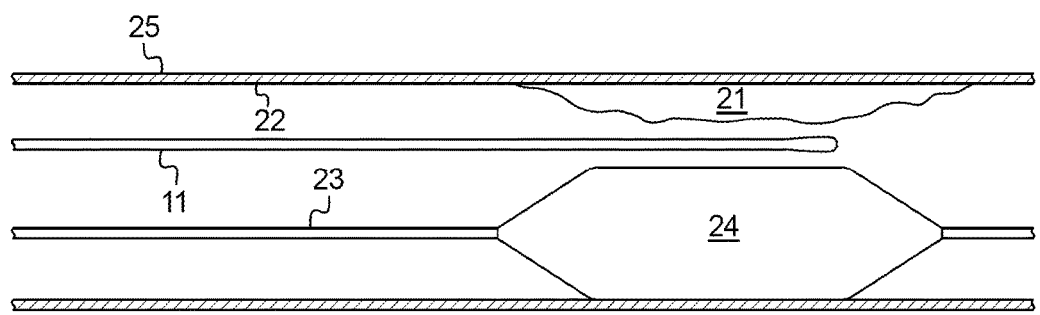
FIG. 2 is a side plan view of a scoring system within an arterial passage, showing a balloon catheter and a wire.

Referring now to the drawings, and particularly to FIGS. 1 and 2, a catheter 23 is shown with a balloon 24 attached. The catheter 23 is inserted into the intraluminal passage 25 in a deflated state. The balloon 24 may be positioned near treatment sites within the passage 25 which are stenotic due to heavy plaque deposits 21 along the wall 22 of the passage. Additionally, a wire 11 is positioned between the balloon 24 and the wall 22 of the intraluminal passage 25. The balloon 24 may then be inflated radially to a certain size and pressure to press the wire 11 against the wall 22 of the intraluminal passage 25.

As shown in FIG. 1, the wire 11 is coupled on its proximal portion to a lithotripter actuator 10. The lithotripter actuator 10 is an energy source capable of creating a mechanical vibration which can be transmitted down the length of the wire 11. In the embodiment shown in FIG. 1, vibration is achieved by depressing a trigger 12 which discharges a Carbon Dioxide ($CO_2$) cartridge 13 and creates a vibration in the wire 11 before passing through a vent 14. The energy source can create the vibration through different methods, however, including use of an electric motor. The vibration can be from a single pulse of mechanical energy or from continuous mechanical energy over a period of time.

As shown in FIG. 2, once the vibration has been transmitted through the wire 11 and reaches the distal end, the wire 11 will impact the plaque 21 as it vibrates. Depending upon the force and the shape of the wire 11 as it impacts the plaque 21, it can fragment plaque 22 causing cracks to form, or compress the plaque 21 against the wall 22 of the passage. Once the vibration of the wire 11 is complete, the vibration may be induced over the same portion again.

After the lithotripter actuator 10 has been activated, the operator of the device may wish to adjust the inflation pressure of the balloon 24 to achieve a different effect with the vibration of the wire 11. If a portion of the plaque 21 lining the wall 22 of the passage 25 has been unaffected by the vibration of the wire 11, it may be due to the force of the wire's 11 vibration being absorbed by contact with the plaque 21 and the proximal portion of the balloon 24. In response, the operator may wish to decrease the inflation pressure of the balloon 24 to increase the length that the mechanical energy is transmitted toward the balloon's 24 distal portion.

Alternatively, after the lithotripter actuator 10 has been activated, the operator of the device may determine that the compression or cracking of the plaque 21 is sufficient in the present treatment site. There may be other treatment sites within the passage 25 where the operator may employ the device. In such a case, the balloon 24 may be deflated, and the device may be rotated, advanced, or partially withdrawn to position the distal portion of the wire 11 between the balloon 24 and another area of plaque 21 lining the wall 22 of the passage 25. Then the balloon 24 may be re-inflated and the lithotripter actuator 10 may be activated again to induce vibration in the distal portion of the wire 11.

The wire 11 can be made of materials capable of easily transmitting vibration, including metals such as stainless steel or nitinol. Furthermore, if the wire 11 is made from a material not visible by x-rays, it may be desirable to place a radiopaque band on the distal portion of the wire 11, so that the operator may determine the wire's 11 position relative to the balloon 24.

In some embodiments, it may be desirable to include an expandable stent. The expandable stent may be arranged on the outer surface 32 of the uninflated balloon 24 in an unexpanded state. Once the balloon 24 has been positioned over the plaque 21, the balloon 24 can be inflated, pressing the expandable stent against the wall 22 of the intraluminal passage 25 and the plaque 21. The wire 11 can then be advanced to a position between the outer surface 32 of the balloon 24 and the inner surface of the expandable stent to transmit vibrations to the stent. Alternatively, the wire 11 may be advanced between the plaque 21 and the outer surface of the expandable stent. Either configuration may be advantageous further expand an expandable stent, pushing further against the plaque 21 or even partially expanding into the plaque 21. Once the expandable stent has been expanded to a sufficient diameter, the balloon 24 may be deflated and the wire 11 and balloon 24 retracted from the intraluminal passage 25, leaving the expandable stent in place. Alternatively, if the expandable stent is made from a material such as nitinol and is heat set in the unexpanded position, when the balloon 24 is deflated, the expandable stent will naturally return to its unexpanded state against the outer surface 32 of the balloon 24. The expandable stent, along with the wire 11 and the balloon 24 may then be retracted from the intraluminal passage 25.

Alternatively, to increase the effectiveness of the wire's 11 transmission of vibrations to the stent, it may be desirable that, while the expandable stent is being advanced to the location of the plaque 21, that the distal portion of the wire 11 is coupled to at least a portion of the expandable stent. This may be accomplished by a latching mechanism on the distal end of the wire 11, or by weaving the distal portion of the wire 11 into the knit of the stent. The wire 11 is advanced with the balloon 24 and the expandable stent. Once the expandable stent is positioned and expanded, the vibration of the wire 11 may be better adapted to transmit vibrations to the stent at the points where the wire 11 is coupled to the expandable stent. Once the desired result is achieved, the wire 11 may be decoupled and retracted from the stent along with the deflated balloon 24.

Figure 3:
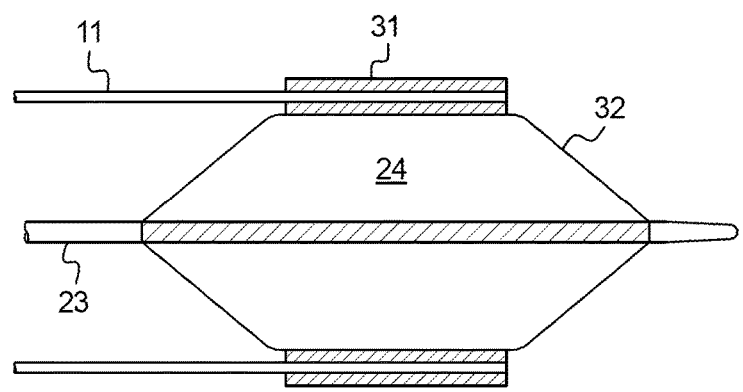
FIG. 3 is a side cross-sectional view of a scoring system, showing a balloon catheter with two wires encased in scoring elements.

Referring now to FIG. 3, another embodiment of the balloon 24 and wires 11 is shown. In contrast to the embodiment shown in FIG. 2, the wire 11 in this embodiment is attached to the balloon 24 through a scoring element 31, which is secured to the balloon's outer surface 32. The wire 11 is encased in the scoring element 31, allowing the mechanical energy from the vibration of the wire 11 to pass through to the scoring element 31, which then impacts plaque 21 lining the passage wall 22.

Scoring elements 31 can be attached to the outer surface 32 of the balloon 24 in multiple ways. An adhesive could be applied between the two contacting surfaces. Alternatively, the scoring element 31 could be partially melted into the outer surface 32 of the balloon 24. As a further alternative, the scoring element 31 could be secured to the outer surface 32 by use of an expanding band which wraps around the outer surface 32 of the balloon 24.

Multiple wires 11 may also be secured to the balloon 24 through scoring elements 31 in FIG. 3. The addition of multiple wires 11 on the outer surface 32 of the balloon 24 allows the scoring device 31 to apply mechanical force to multiple areas of the intraluminal passage simultaneously.

Figure 4:
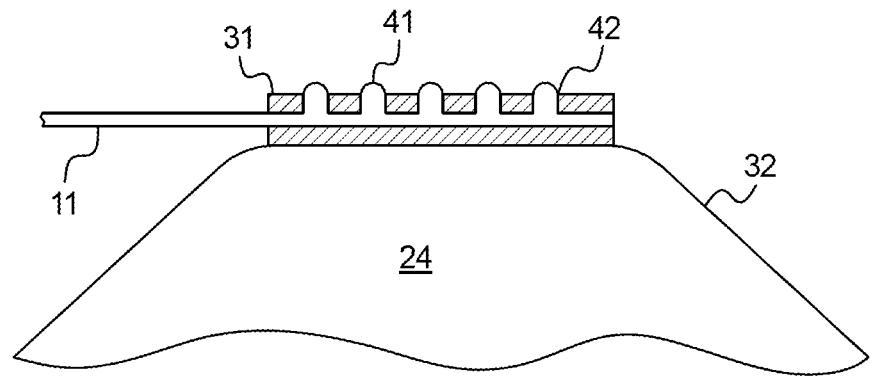
FIG. 4 is a side cross-sectional view of a scoring element, showing the wire with projections encased within the scoring element.

Referring now to FIG. 4, another embodiment of the scoring element 31 and wire 11 is shown. In this embodiment, the wire 11 is held in place within the scoring element 31 through one or more projections 41 extending radially from the wire 11 through a matching number of openings 42 on the scoring element. These projections 41 can have the effect of directing the force of the wire's 11 impact onto smaller areas of the plaque 21, causing better compression of plaque 21 against the wall 22 of the passage 25 or causing fragmentation of the plaque 21.

Figure 5:
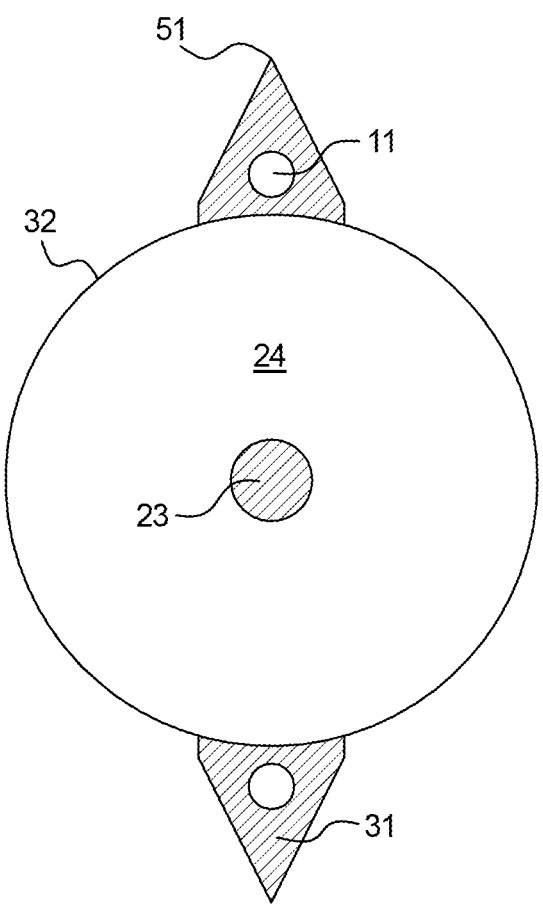
FIG. 5 is a lateral cross-sectional view of the scoring system, showing a scoring element with an outer edge.
Figure 6:
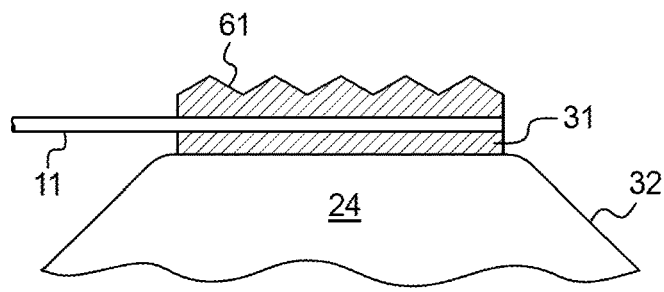
FIG. 6 is a side cross-sectional view of a scoring element, showing a wire encased within a scoring element with a shaped edge.

Referring now to FIGS. 5 and 6, another embodiment of the scoring element 31 is shown. In this embodiment, each scoring element 31 has an edge 51 extending out from the outer surface 32 of the balloon 24. This edge 51 may be used to enhance the effect of vertical vibrations in the wire 11 and cause targeted compressions or cracking in the plaque 21 lining the walls 22 of the passage 25. In an alternative embodiment, the edge 51 might have a varying height profile 61 with respect to the edge's 51 longitudinal position along the scoring element 31. An edge 51 with a varying height profile 61 as shown in FIG. 6 may be used to enhance the effect of both vertical and longitudinal vibrations in the wire 11 and cause compression or fragmentation of the plaque 21 lining the walls 22 of the passage 25.

Figure 7:
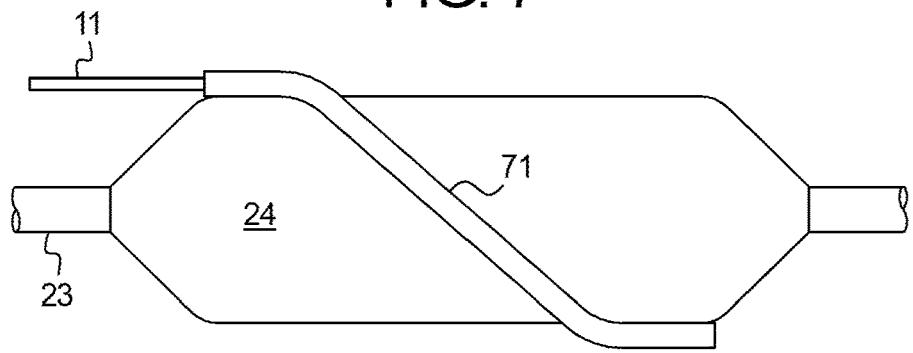
FIG. 7 is a side plan view of a scoring system, showing a balloon catheter with a wire and a scoring element curved around the outer surface of the balloon.

Referring now to FIG. 7, another embodiment of the scoring element 71 and balloon 24 is shown. In contrast to the embodiments shown in FIGS. 1, 5, and 6, this embodiment shows a scoring element 71 which is curved around the outer surface 32 of the balloon 24. The curve of the element 71 can allow the scoring element 71 to transmit the force of the vibration in lateral, longitudinal, and circumferential directions, allowing more efficient compression or cracking of the plaque 21 lining the walls 22 of the passage 25.

In order to secure the curved element 71 of this embodiment to the outer surface 32, it may be necessary to encase the scoring element 71 between two layers of the balloon 24 material during manufacture. The inner layer would form the surface of a normal inflatable balloon 24 with the curved element 71 resting on its outer surface 32. The outer layer would lay along the top of the entire length the element 71 and would be melted into the inner layer to secure the element 71 in place. The presence of the element 71 would still allow the balloon 24 to have a curved projection extending radially from its outer surface 32.

Figure 8:
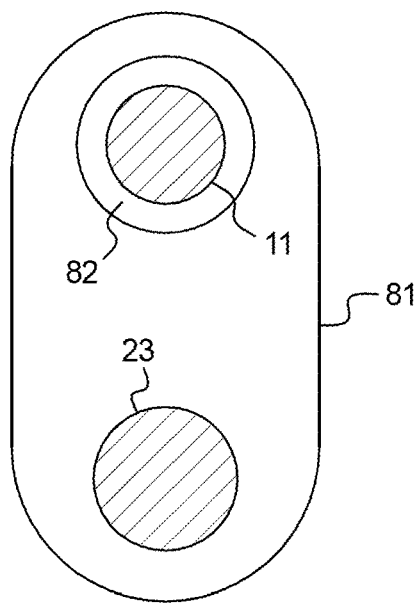
FIG. 8 is a lateral cross-sectional view of a catheter adjacent to the proximal end of the balloon, showing a collar coupled to the catheter and a wire passing through the collar.

Referring now to FIG. 8, another embodiment of the wire 11 and balloon 24 is shown with the addition of a collar 81. The collar 81 is positioned adjacent to the proximal end of the balloon 24 and may be attached to the balloon 24 or catheter 23. The wire 11 passes through a hole 82 in the collar 81, coupling the wire 11 to the catheter 23. The collar 81 prevents the wire 11 from impacting portions of the passage 25 before the vibration reaches the distal end. The hole 82 that the wire 11 passes through preferably is large enough to allow the vibration of the wire 11 to pass through the wire 11 towards the distal end. If the hole 82 of the collar 81 fits too closely around the wire 11, too large a portion of the mechanical energy of the vibration may be lost.

Referring now to FIG. 9, another embodiment of the wire 11 and balloon 24 is shown with the addition of an embolic protection system 91. The embolic protection system 91 consists of a device, such as a net or another balloon, which is placed downstream from the balloon 24 and wire 11. The system should be deployed prior to activation of the lithotripter actuator 10. Once deployed, the embolic protection device 91 blocks the flow of blood, or filters the blood to prevent any embolisms that might occur as a result of fragmentation of plaque 21 along the walls 22 of the passage 25.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:

1. An intraluminal scoring system comprising:
    a balloon comprising an outer surface, a proximal portion, and a distal portion, wherein the proximal and distal portions are attached to a catheter, and wherein the outer surface inflates radially from the catheter;
    a wire comprising proximal and distal portions, wherein the distal portion of the wire extends along the outer surface of the balloon;
    a scoring element comprising a contacting surface directly secured to the outer surface of the balloon, wherein the distal portion of the wire is enclosed within the scoring element, and the distal portion of the wire comprises a projection extending radially through an opening on the scoring element; and
    a lithotripter coupled to the proximal portion of the wire, wherein the lithotripter may be activated to transmit mechanical energy from the lithotripter, through the wire to vibrate the distal portion of the wire.

2. The intraluminal scoring system of claim 1, wherein the scoring element is secured to the outer surface of the balloon by melting the scoring element into the outer surface of the balloon.

3. The intraluminal scoring system of claim 1, wherein the scoring element further comprises an edge, extending out from the outer surface of the balloon.

4. The intraluminal scoring system of claim 3, wherein the edge of the scoring element has a varying height profile along the length of the balloon.

5. The intraluminal scoring system of claim 1, wherein the scoring element extends generally straight along the outer surface of the balloon.

6. The intraluminal scoring system of claim 1, wherein the scoring element is curved around the outer surface of the balloon.

7. The intraluminal scoring system of claim 1, wherein the lithotripter is activated by the discharge of a $CO_2$ cartridge.

8. The intraluminal scoring system of claim 1, further comprising a collar adjacent to the proximal portion of the balloon, wherein the wire passes through the collar.

9. The intraluminal scoring system of claim 1, further comprising an expandable stent positioned on the outer surface of the balloon, wherein the distal portion of the wire is in contact with at least a portion of the expandable stent.

10. A method of scoring an intraluminal passage, comprising:
    positioning a scoring device in an intraluminal passage, wherein the scoring device comprises:
        a catheter;
        a balloon attached to the catheter, wherein the balloon has an outer surface which can be inflated radially from the catheter, and a scoring element comprising a contacting surface directly secured to an outer surface of the balloon;
        a wire comprising proximal and distal portions, wherein the distal portion of the wire is enclosed within the scoring element, and the distal portion of the wire comprises a projection extending radially through an opening on the scoring element, and
        a lithotripter comprising an energy source, wherein the proximal portion of the wire is coupled to the lithotripter;
    positioning the balloon at a treatment site in a deflated state;
    inflating the balloon, thereby constraining the wire between the balloon and a wall of the intraluminal passage;
    actuating the lithotripter, thereby transmitting mechanical energy from the lithotripter through the wire in response to the actuation; and
    impacting plaque lining the wall of the intraluminal passage with the scoring element in response to the mechanical energy transmitted from the lithotripter.

11. The method of claim 10, further comprising further inflating the balloon after actuation of the lithotripter, allowing the balloon and the wire to thereby apply additional force to the wall of the intraluminal passage.

12. The method of claim 11, further comprising actuating the lithotripter a second time after the balloon has been further inflated.

13. The method of claim 10, further comprising decreasing the inflation pressure of the balloon after actuating the lithotripter, thereby increasing the length that the mechanical energy may be transmitted toward a distal portion of the balloon.

14. The method of claim 13, further comprising:
   deflating the balloon;
   rotating the scoring element within the intraluminal passage; and
   repeating the step of inflating the balloon and actuating the lithotripter.

15. The method of claim 10, wherein the scoring system further comprises a collar adjacent to a proximal portion of the balloon, wherein the wire passes through the collar.

16. The method of claim 10, further comprising deploying an embolic protection device downstream from the balloon prior to transmitting mechanical energy through the wire.

17. An intraluminal scoring system comprising:
   a balloon comprising an outer surface, a proximal portion, and a distal portion, and a scoring element coupled to the outer surface of the balloon, wherein the proximal and distal portions are attached to a catheter, and the outer surface inflates radially from the catheter;
   a wire comprising proximal and distal portions, wherein the distal portion of the wire comprises a projection extending radially through an opening on the scoring element; and
   a lithotripter coupled to the proximal portion of the wire, the lithotripter comprising a gas cartridge, wherein discharge of the gas cartridge transmits a vibration through the wire to the distal portion of the wire.

18. The intraluminal scoring system of claim 17, wherein the gas cartridge contains compressed carbon dioxide gas.

19. The intraluminal scoring system of claim 17, wherein the lithotripter further comprises a vent to allow gas discharged from the gas cartridge to exit the lithotripter.

20. The intraluminal scoring system of claim 17, wherein the distal portion of the wire comprises a plurality of projections, each of the plurality of projections extending radially through one of a plurality of openings on the scoring element.

21. The intraluminal scoring system of claim 17, wherein a position of the projection within the opening on the scoring element is adapted to restrict retraction of the wire through the scoring element.

* * * * *